United States Patent [19]

Baines et al.

[11] 4,123,517

[45] Oct. 31, 1978

[54] TOOTHPASTE COMPOSITIONS

[75] Inventors: Eric Baines, Flixton; Kenneth Harvey, Wilmslow, both of England

[73] Assignee: Colgate-Palmolive Company, New York, N.Y.

[21] Appl. No.: 645,743

[22] Filed: Dec. 31, 1975

[30] Foreign Application Priority Data

Jan. 15, 1975 [GB] United Kingdom ............... 1798/75

[51] Int. Cl.² .......................... A61K 7/16; A61K 7/18
[52] U.S. Cl. ...................................... 424/57; 424/49; 424/52; 424/54
[58] Field of Search ..................................... 424/49–58

[56] References Cited

U.S. PATENT DOCUMENTS

| | | | |
|---|---|---|---|
| 3,034,967 | 5/1962 | Apperson et al. | 424/52 |
| 3,060,098 | 10/1962 | Gerson | 424/52 |
| 3,227,617 | 1/1966 | Manahan et al. | 424/49 |
| 3,227,618 | 1/1966 | Manahan et al. | 424/49 |
| 3,662,060 | 5/1972 | Clippendale et al. | 424/57 |
| 3,670,076 | 6/1972 | Muhler | 424/49 |
| 3,678,155 | 7/1972 | Clippendale et al. | 424/49 |
| 3,822,345 | 7/1974 | Murray et al. | 424/52 |
| 3,937,805 | 2/1976 | Harrison | 424/52 |
| 3,956,478 | 5/1976 | King et al. | 424/52 |
| 3,957,968 | 5/1976 | Cordon et al. | 424/49 |

*Primary Examiner*—Shep K. Rose
*Attorney, Agent, or Firm*—Robert L. Stone; Murray M. Grill; Herbert S. Sylvester

[57] ABSTRACT

Toothpaste composition having desirable compatibility with an unlimited aluminum container, which toothpaste contains a polishing material comprising hydrate of alumina and an anionic phosphate mono- or di-ester.

7 Claims, No Drawings

TOOTHPASTE COMPOSITIONS

This invention relates to a toothpaste composition. In particular it relates to a toothpaste composition which is compatible with an unlined aluminium container such as a toothpaste tube.

Hydrated alumina such as alpha alumina trihydrate (e.g. Gibbsite) is a desirable polishing agent for dental surfaces and has been incorporated into toothpaste compositions. The alkalinity of hydrated alumina is such that when a toothpaste containing it is incorporated into an unlined aluminium container such as a toothpaste tube, gas formation, causing container swelling, often occurs as does etching of the aluminium surface.

It is an advantage of this invention that a toothpaste composition is provided which contains hydrated alumina as polishing agent and a particular anionic foaming surface active agent which permits the use of the toothpaste composition in an unlined aluminium container without undue incompatibility.

In accordance with certain of its aspects this invention relates to a toothpaste composition comprising a dentally acceptable oral vehicle and dispersed therein about 20 – 75% by weight of a polishing material including hydrate of alumina in amount of at least 10% by weight of the toothpaste, and about 0.05 – 5% by weight of an anionic phosphate ester surface active agent comprising a mixture of monoester of the formula

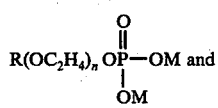

and
diester of the formula

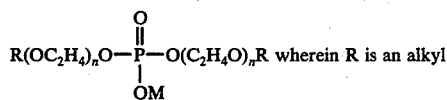

wherein R is an alkyl group of 10–20 carbon atoms, $n$ is an integer from 1–6 and M is selected from the group consisting of hydrogen, alkali metal and ammonium, said toothpaste having a pH of up to about 9.5.

In accordance with certain of its additional aspects, this invention relates to a packaged toothpaste composition comprising an unlined aluminium container and contained therein in contact with the aluminium surface of said container the above described toothpaste composition.

The hydrated alumina employed is an alpha alumina trihydrate. A conventional way of manufacturing this material is by the Bayer process. In that process the alpha alumina trihydrate is precipitated from a solution of sodium aluminate. See Encyclopedia of Chemical Technology, Kirk-Othmer, 2nd. Edition, Vol. 1, pages 937–941, and Vol. 2, pages 41–45 and 50–51. The trihydrate compound is precipitated in the form of granules or agglomerates which are too large for general use as a dentifrice polishing material, e.g. about 40 to 100 microns diameter. Therefore the granules or agglomerates, after drying (sometimes after water-washing and drying) are ground to a suitable particle size, e.g. to an average particle diameter in the range of about 2 to 20 microns, such as about 5 to 10 microns in diameter.

The washed unground granules usually show an alkaline reaction when slurried in water. For instance, depending on the degree of washing before drying, the pH of a 10% or 20% by weight of trihydrate slurry at room temperature may be in the range of about 7.5, 8.5, 9 or 9.5.

The pH can be measured with an Orion model 801 Digital pH/mv meter which is fitted with an EIL model 1150 combination pH and reference electrode. The instrument is first calibrated at room temperature by placing the electrode into 50 ml of pH 7 buffer solution in a 100 ml beaker, and adjusting the calibration control until the instrument reading corresponds to a buffer pH. The electrode is then removed, washed with deionized water, and placed into 125 gms of a pre-prepared 20% slurry of the trihydrate sample in deionized water, in a 250 ml beaker, and its pH reading taken.

On grinding the alkalinity thus measured increases and the pH (measured as above) of the ground, unwashed material is generally above about 8. For instance the pH on grinding may change as follows: 7.5 (before grinding) to 8.8 (after grinding); 8.8 (before) to 9.2 (after). The bulletin of one manufacturer gives the pH of a 10% slurry, in water, of the ground material as 8.8 – 10.6. When such ground trihydrate is included in a dentifrice packaged in unlined aluminium tubes, one often observes swelling of the tubes or other evidence of gas formation resulting from attack on the aluminium (e.g. forming hydrogen gas) on extended storage.

The anionic phosphate esters are mixtures of mono and di-esters of the formulas hereinabove set forth. They are available from MoDo Kemi Aktiebolaget, formerly Berol Aktiebolaget, of Sweden, under the name Berol and may include an anionic tri-ester moiety too, as well as some non-ionic portion. They may be used in acid or partially or fully neutralised forms. Berol 729 has alkyl chain lengths of 16–18 carbon atoms and contains series of 4 ethylene oxide units.

Further anionic phosphate esters which may be used in acid or neutralised forms are Berol 525 which contains alkyl groups of 10–18 carbon atoms and series of 5 ethylene oxide units and Berol 513 which contains alkyl groups of 16–18 carbon atoms. Further Berol anionic phosphate esters are available as Berol 521, Berol 724 and Berol 733. The weight ratio of mono-ester to di-ester may vary, typically from about 1:10 to 10:1.

When the acid forms of the anionic phosphate ester surface active agents are neutralised or partially neutralised, alkali metal, preferably sodium, or ammonium cations are present. The surface active agent is employed in the oral preparation in amount of about 0.05-5% by weight, preferably about 0.5-3% and most preferably about 0.5-2%. The phosphate esters serve to improve dentifrice consistency and body.

The toothpaste may comprise an additional dentally acceptable water-insoluble polishing material, such as calcined alumina, dehydrated silica, crystalline silica, having particles of sizes up to about 5 microns, a mean particle size of up to 1.1 microns and a surface area of up to 50,000 cm$^2$/gm, water-insoluble sodium metaphosphate (preferably substantially free of water-solubles content), tricalcium phosphate, dihydrated dicalcium phosphate, anhydrous dicalcium phosphate, calcium pyrophosphate, magnesium orthophosphate, trimagnesium phosphate, calcium carbonate, aluminium silicate, zirconium silicate, bentonite and mixtures thereof. At least 10% of the toothpaste is hydrated alumina.

The polishing material is generally present in amounts of about 20–75% by weight of a toothpaste containing it, about 30–55% being preferable. Preferably about 20–55% of the toothpaste is hydrated alumina.

In toothpaste preparations, the liquid vehicle may comprise water, typically in amount of about 10–90% by weight of the preparation. The liquid vehicle may additionally or alternatively comprise humectants such as glycerine, sorbitol solution propylene glycol. A mixture of water and glycerine and/or sorbitol solution is particularly advantageous. Preferably about 20–40% by weight of humectant and 10 to about 45% by weight of water is present.

The solid portion of the vehicle of a paste or gel composition is a gelling agent or binder such as hydroxyethyl cellulose and hydroxypropyl cellulose. These gelling agents are particularly preferred since they do not provide ions to the composition. Other gelling agents which may be used include Irish moss, gum tragacanth, sodium carboxymethyl cellulose, polyvinyl pyrrolidone, starch and water-soluble hydrophilic colloidal carboxyvinyl polymers such as those sold under the name Carbopol 934 and 940.

The toothpaste is placed in an extrudable tube of unlined aluminium for easy application to a toothbrush.

The toothpastes may include an organic surface active agent in addition to the anionic phosphate ester surface active agent. Such additional agent may be anionic, nonionic, cationic or ampholytic in nature, and it is preferred to employ as the surface-active agent a detersive material which imparts to the dentifrice detersive and foaming properties. Suitable types of such detergents are water-soluble salts of higher (i.e. having at least 12 carbon atoms) fatty acid monoglyceride monosulphates, such as the sodium salt of the monosulphated monoglyceride of hydrogenated coconut oil fatty acids, high alkyl sulphates, such as sodium lauryl sulphate, alkyl aryl sulphonates, such as sodium dodecyl benzene sulphonate, olefin sulphonates, such as sodium olefin sulphonate in which the olefin group contains 12–21 carbon atoms, higher alkyl sulphoacetates, higher fatty acid esters of 1,2-dihydroxy propane sulphonates, and the substantially saturated higher aliphatic acyl amides of lower (i.e. having not more than 4 carbon atoms) aliphatic amino carboxylic acid compounds, such as those having 12–16 carbons in the fatty acid, alkyl or acyl radicals. Examples of the last mentioned amides are N-lauroyl sarcosine, and the sodium, potassium and ethanolamine salts of N-lauroyl, N-myristoyl or N-palmitoyl sarcosine, which should be substantially free from soap or similar higher fatty acid material which tends to substantially reduce the effect of these compounds. The use of these sarcosine compounds in dentifrices is particularly advantageous since these materials exhibit a prolonged and marked effect in the inhibition of acid formation in the oral cavity due to carbohydrates breakdown in addition to exerting some reduction in the solubility of tooth enamel in acid solutions.

Other particularly suitable surface-active materials include nonionic agents such as condensates of sorbitan monostearate with approximately 60 moles of ethylene oxide, condensates of ethylene oxide with propylene oxide condensates of propylene glycol ("Pluronics"—PLURONIC is a Trade Mark) and amphoteric agents such as quaternised imidazole derivatives, which are availabe under the trade name "Miranol" such as Miranol C2M. Cationic surface active germicides and antibacterial compounds such as diisobutylphenoxyethoxyethyl dimethyl benzyl ammonium chloride, benzyl dimethyl stearyl ammonium chloride, tertiary amines having one fatty alkyl group (of from 12–18 carbon atoms) and two (poly) oxyethylene groups attached to the nitrogen (typically containing a total of from 20 to 50 ethanoxy groups per molecule) and salts thereof with acids, and compounds of the structure

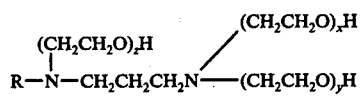

wherein R is a fatty alkyl group typically containing from 12 to 18 carbon atoms, and $x$, $y$ and $z$ total 3 or higher, as well as salts thereof with mineral or organic acids, may also be used. It is preferred that the total amount of surface active agent not exceed about 5% by weight of the oral composition. At least about 0.05% of the oral composition should be composed of the anionic phosphate ester surface active agent.

In certain forms of this invention a fluorine-providing compound is present in the oral preparation. These compounds may be slightly soluble in water or may be fully water-soluble. They are characterised by their ability to release fluoride ions in water and by substantial freedom from reaction with other compounds of the oral preparation. Among these materials are inorganic fluoride salts, such as suitable alkali metal, alkaline earth metal, and heavy metal salts, for example, sodium fluoride, potassium fluoride, ammonium fluoride, a copper fluoride such as cuprous fluoride, zinc fluoride, a tin fluoride such as stannic fluoride, or stannous chlorofluoride, barium fluoride, sodium fluorosilicate, ammonium fluorosilicate, sodium fluoro-zirconate, sodium monofluorophosphate, aluminium mono- and di-fluorophosphate, and fluorinated sodium calcium pyrophosphate. Alkali metal and tin fluorides, such as sodium and stannous fluorides and particularly sodium monofluorophosphate are preferred.

The amount of the fluorine-providing compound is dependent to some extent upon the type of compound, its solubility, and the type of oral preparation, but it must be a non-toxic amount. It is considered that an amount of such compound which releases a maximum of 1% by weight, based on the weight of the preparation, is satisfactory. Any suitable minimum amount of such compound may be used, but it is preferable to employ sufficient compound to release from 0.005% to 1%, most preferably about 0.1%, by weight of fluoride ion. Typically, in the cases of alkali metal fluoride and stannous fluoride, this component is present in an amount up to 2% by weight, based on the weight of the preparation, and preferably in the range of from 0.05% to 1%. In the case of sodium monofluorophosphate the compound may be present in an amount up to 7.6% by weight, more typically 0.76%.

Antibacterial agents may also be present, typically in an amount of 0.01–5% by weight. Typical antibacterial agents include $N^1$-(4-chlorobenzyl)-$N^5$-(2,4-dichlorobenzyl)biguanide;
p-chlorophenyl biguanide;
4-chlorobenzhydryl biguanide;

4-chlorobenzhydrylguanylurea;
N-3-lauroxypropyl-N⁵-p-chlorobenzylbiguanide;
1,6-di-p-chlorophenylbiguanidohexane; (chlorohexidine);
1,6-bis(2-ethylhexylbiguanido)hexane;
1-(lauryldimethylammonium)-8-(p-chlorobenzylidimethylammonium) octane dichloride;
5,6-dichloro-2-guanidinobenzimidazole;
N¹-p-chlorophenyl-N⁵-laurylbiguanide;
5-amino-1,3-bis(2-ethylhexyl)-5-methylhexahydro pyrimidine; and their non-toxic acid addition salts.

Various other materials may be incorporated in the oral preparations of this invention. Examples are colouring or whitening agents, preservatives, silicones, chlorophyll compounds, and ammoniated material such as urea, diammonium phosphate, and mixtures thereof. These adjuvants, where present, are incorporated in the preparations in amounts which do not substantially adversely affect the properties and characteristics desired.

Any suitable flavouring or sweetening materials may also be employed. Examples of suitable flavouring constituents are flavouring oils, e.g. oils of spearmint, peppermint, wintergreen, sassafras, clove, sage, eucalyptus, marjoram, cinnamon, lemon and orange, and methylsalicylate. Suitable sweetening agents include sucrose, lactose, maltose, sorbitol, sodium cyclamate, perillartine, and saccharin. Suitably, flavour and sweetening agent may together comprise from 0.01% to 5% or more of the preparation.

The toothpaste typically has a pH of about 4 – 10, preferably about 5 – 9. When reference is made to the pH herein, it is intended that the pH determination be made directly on the toothpaste.

The toothpastes are typically prepared by dispersing polishing material in the dental vehicle and adding the phosphate ester and other components thereto.

The following specific examples are further illustrative of the nature of the present invention although it is understood that the invention is not limited thereto. All amounts are by weight unless otherwise indicated.

EXAMPLE 1

The following toothpastes are prepared by mixing gelling agent and sweetener with humectant, thereafter adding polishing agent, whitener, water and surface-active agent, and finally flavour. The toothpastes are deaerated and placed in unlined aluminium tubes.

|  | Parts by weight |
|---|---|
| Glycerine | 20.00 |
| Hydroxyethyl Cellulose | 1.30 |
| Sodium Saccharine | 0.20 |
| Titanium Dioxide | 0.50 |
| Water | 24.00 |
| Alpha Alumina Trihydrate (British Aluminium AF 260) | 51.50 |
| Phosphate Ester (as indicated below) | 1.50 |
| Flavour | 1.00 |

The following phosphate esters are employed, resulting in toothpastes having the pH valves indicated:

| Phosphate Ester | Toothpaste pH |
|---|---|
| Berol 513 (acid form) | 6.3 |
| Berol 525 (acid form) | 5.4 |
| Berol 521 (acid form) | 9.5 |
| Berol 729 (acid form) | 3.7 |

| Phosphate Ester | Toothpaste pH |
|---|---|
| Berol 729 (fully neutralised) | 9.1 |

The toothpastes remain satisfactorily compatible with the unlined aluminium tubes which contain them upon storage for 6 months at room temperature, at accelerated aging conditions of 43° C. for 3 months.

Similar desirable tube compatibility occurs when the Berol phosphate esters are used in their fully neutralised or partially neutralised forms in place of the acid forms.

Likewise desirable tube compatibility occurs when the above toothpaste formulation containing the various phosphate esters includes 4.723 parts of 1,6-di-(p-chlorophenyl biguanido)hexane digluconate (20% soln) in one set of cases or 0.76 parts of sodium monofluorophosphate in another set of cases, with the formula amount of water being correspondingly reduced.

EXAMPLE 2

The following toothpaste is prepared, deaerated and placed in unlined aluminium tubes:

|  | Parts by weight |
|---|---|
| Glycerine | 20.202 |
| Sodium Carboxymethyl Cellulose | 1.10 |
| Water | 27.16 |
| Sodium Saccharine | 0.20 |
| Alpha Alumina Trihydrate (British Aluminium AF 260) | 52.00 |
| Titanium Dioxide | 0.5 |
| Sodium N-Lauroyl Sarcosinate | 1.538 |
| Berol 513 (Partially neutralised form) | 0.50 |
| Flavour | 0.80 |
| Toothpaste pH 7.2 | |

The toothpaste remains compatible with the aluminium tube upon accelerated aging for 3 months at 43° C. as well as upon aging at room temperature for 3 months.

The foregoing examples are given by way of illustration and variations may be made without departing from the spirit of the invention.

What we claim is:

1. A toothpaste comprising a dentally acceptable oral vehicle and dispersed therein about 20–75% by weight of a polishing material including ground alpha-alumina trihydrate having an average particle diameter in a range of about 2 to 20 microns wherein the pH of a 10–20% by weight of a slurry of the alpha alumina trihydrate prior to grinding is in the range of about 7.5–9.5 and the pH of such a slurry after said grinding is higher than before grinding and is above 8, said alpha alumina trihydrate being present in amount of at least 10% by weight of the toothpaste, and about 0.5–3% by weight of an anionic phosphate ester surface active agent comprising a mixture of mono ester of the formula

$$R(OC_2H_4)_n OP(=O)(OM)_2$$ and diester of the formula

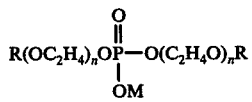

$$R(OC_2H_4)_n OP(=O)(OM)-O(C_2H_4O)_n R$$

wherein R is an alkyl group of 10 – 20 carbon atoms, n is an integer from 1 – 6 and M is selected from the group consisting of hydrogen, alkali metal and ammonium, said toothpaste having a pH toothpaste of about 5 - 9, said anionic phosphate ester surface active agent being effective to provide consistency and body to said toothpaste and render said toothpaste compatible with an unlined aluminum container.

2. The toothpaste claimed in claim 1 wherein said anionic phosphate ester contains 16–18 carbon atoms.

3. The toothpaste claimed in claim 2 wherein R in said anionic phosphate ester contains a series of four ethylene oxide units.

4. The toothpaste claimed in claim 1 wherein said anionic phosphate ester contains 10 - 18 carbon atoms and R in said anionic phosphate ester contains a series of five ethylene oxide units.

5. The toothpaste claimed in claim 1 wherein the ratio of mono-ester to di-ester in said anionic phosphate ester varies from about 1:10 to 10:1 by weight.

6. The toothpaste claimed in claim 1 wherein said anionic phosphate ester is present in amount of about 0.5–2% by weight.

7. A packaged toothpaste wherein the toothpaste of claim 1 is in an unlined aluminium container and in contact with the aluminium surface of said container.

* * * * *